United States Patent
Onuki

(10) Patent No.: US 11,241,426 B2
(45) Date of Patent: Feb. 8, 2022

(54) AQUEOUS COMPOSITION FOR OPHTHALMIC OR NASAL ADMINISTRATION

(71) Applicant: NITTO MEDIC CO., LTD., Toyama (JP)

(72) Inventor: Mineo Onuki, Toyama (JP)

(73) Assignee: Nitto Medic Co., Ltd., Toyama (JP)

( * ) Notice: Subject to any disclaimer, the term of this patent is extended or adjusted under 35 U.S.C. 154(b) by 0 days.

(21) Appl. No.: 16/484,957

(22) PCT Filed: Feb. 9, 2018

(86) PCT No.: PCT/JP2018/004572
§ 371 (c)(1),
(2) Date: Oct. 7, 2019

(87) PCT Pub. No.: WO2018/147409
PCT Pub. Date: Aug. 16, 2018

(65) Prior Publication Data
US 2020/0030320 A1    Jan. 30, 2020

(30) Foreign Application Priority Data

Feb. 13, 2017    (JP) .............................. JP2017-024313

(51) Int. Cl.
| | | |
|---|---|---|
| *A61K 31/495* | (2006.01) |
| *A61P 27/14* | (2006.01) |
| *A61P 11/02* | (2006.01) |
| *A61K 9/00* | (2006.01) |
| *A61K 9/08* | (2006.01) |

(52) U.S. Cl.
CPC .......... *A61K 31/495* (2013.01); *A61K 9/0043* (2013.01); *A61K 9/0048* (2013.01); *A61K 9/08* (2013.01); *A61P 11/02* (2018.01); *A61P 27/14* (2018.01)

(58) Field of Classification Search
CPC ...... A61K 31/495; A61K 9/08; A61K 9/0048; A61K 9/0043; A61K 47/26; A61K 47/12; A61P 11/02; A61P 27/14; A61P 43/00; A61P 37/08
See application file for complete search history.

(56) References Cited

U.S. PATENT DOCUMENTS

| | | |
|---|---|---|
| 5,419,898 A | 5/1995 | Ikejiri et al. |
| 6,319,927 B1 | 11/2001 | Martin |
| 2011/0257136 A1* | 10/2011 | Abelson .................. A61P 27/16 514/171 |

FOREIGN PATENT DOCUMENTS

| | | |
|---|---|---|
| JP | H06-239748 | 8/1994 |
| JP | 2004-168709 | 6/2004 |

(Continued)

OTHER PUBLICATIONS

Xyzal-WebMD citation (Year: 2020).*

(Continued)

*Primary Examiner* — Carlos A Azpuru
(74) *Attorney, Agent, or Firm* — Sheridan Ross P.C.

(57) ABSTRACT

Provided is an aqueous composition for ophthalmic or nasal administration comprising levocetirizine or its salt. In one embodiment, the composition comprises levocetirizine or its salt at a levocetirizine concentration of 0.05-0.5% (w/v). The composition may further comprise a surface active agent and/or an organic acid salt.

13 Claims, 1 Drawing Sheet

(56) References Cited

FOREIGN PATENT DOCUMENTS

| JP | 2008-505949 | | 2/2008 |
|---|---|---|---|
| JP | 2008505949 | * | 2/2008 |
| JP | 2012-520882 | | 9/2012 |

OTHER PUBLICATIONS

TERASHI "Regarding novel drugs for separating optical isomer," Journal of the Kagoshima City Medical Association, 2012, vol. 51, No. 8, pp. 78-79.
International Preliminary Report on Patentability for International (PCT) Patent Application No. PCT/JP2018/004572, dated Aug. 22, 2019, 10 pages.
International Search Report prepared by the Japan Patent Office dated Feb. 26, 2018, for International Application No. PCT/JP2018/004572.
"Polysorbate 80 Monograph," The United States Pharmacopeial Convention, 2015, 3 pages.

* cited by examiner

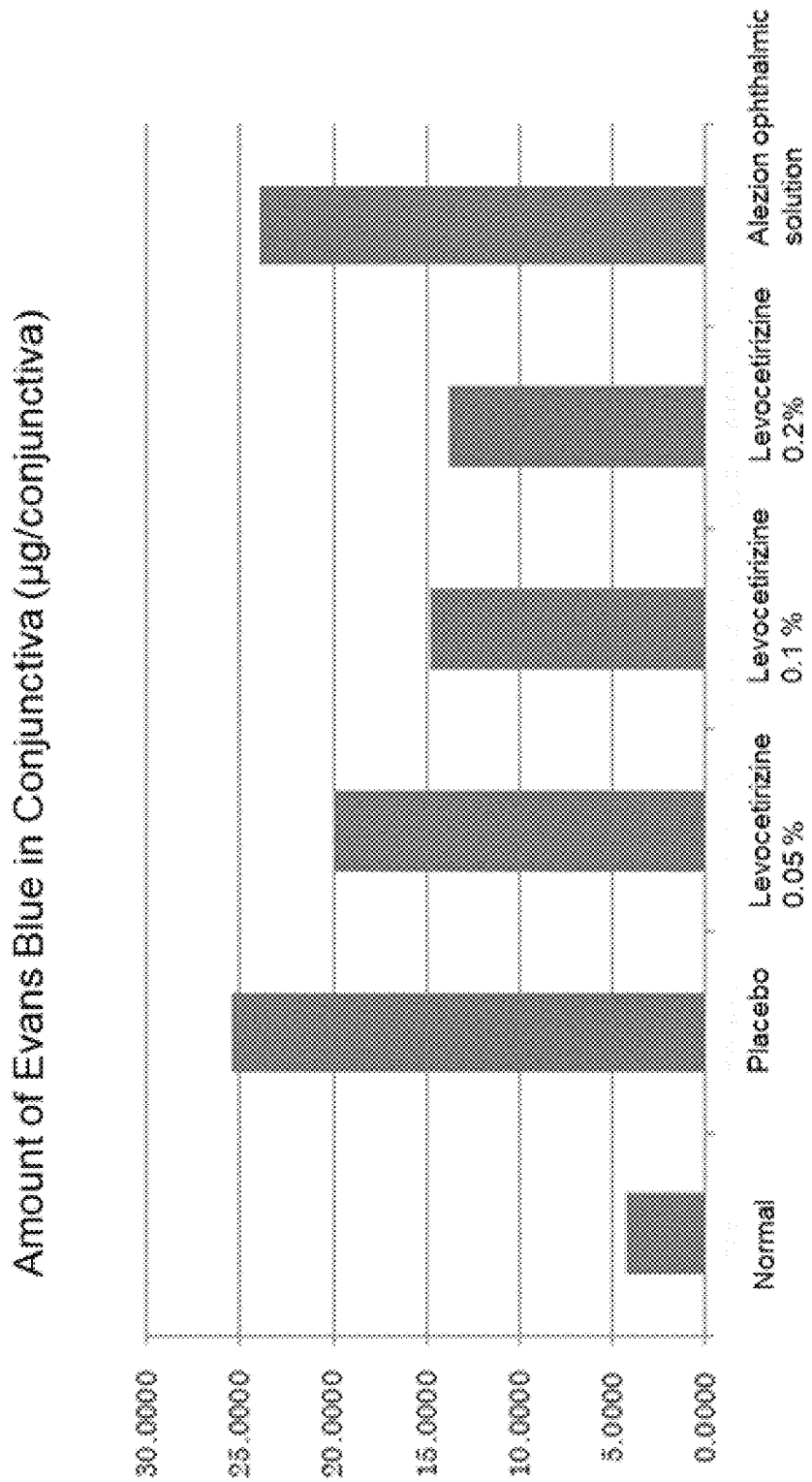

AQUEOUS COMPOSITION FOR OPHTHALMIC OR NASAL ADMINISTRATION

CROSS REFERENCE TO RELATED APPLICATIONS

This application is a national stage application under 35 U.S.C. 371 and claims the benefit of PCT Application No. PCT/JP2018/004572 having an international filing date of 9 Feb. 2018, which designated the United States, which PCT application claimed the benefit of Japan Patent Application No. 2017-024313 filed 13 Feb. 2017, the disclosures of each of which are incorporated herein by reference in their entireties.

TECHNICAL FIELD

The present application relates to an aqueous composition comprising levocetirizine for ophthalmic or nasal administration.

BACKGROUND ART

Levocetirizine is the R-enantiomer of a racemic compound, cetirizine. It has been known as a potent histamine receptor antagonist having an affinity for the human H1 receptor that is about 2-fold higher than that of cetirizine and is about 30-fold higher than that of the S-enantiomer, dextrocetirizine. Levocetirizine has been developed as an active ingredient of orally administered second-generation antihistamine medicaments and used for the treatment of allergic rhinitis and dermatosis.

Allergic dermatosis are often associated with systemic symptoms and can effectively be treated by oral antihistamines. Allergic ocular diseases, on the other hand, may be associated solely ocular local symptoms are often not accompanied by systemic symptoms. Local treatment of the eyes by an ophthalmic composition will be safer and more effective than systemic treatment by orally administered medicaments that could have risk of systemic side effects. Similarly, demands for medicaments that are administered to nose are desired for treating nose allergies.

In general, formulation of an ophthalmic or nasal solution is determined by solubility and stability of the active ingredient in water. The formulation may comprise various additives in addition to the active ingredient. Ingredients in a formulation interact each other in a complex way, and the solubility, stability and safety of each ingredient may be affected by the type and amount of the active ingredient and additives. Determination of the final formulation is not easy.

For example, benzalkonium chloride, which is a widely used preservative and also functions as a solubilizer, is also known to cause corneal disorder.

SUMMARY OF INVENTION

Problem to be Solved by Invention

Levocetirizine is extremely unstable, especially unstable in its physiochemical properties. For example, the compound in an aqueous solution crystallizes and precipitates over time, causes irritation and is easily degraded due to oxidization. The compound is difficult to be formulated as an aqueous formulation. There is no stable and safe ophthalmic or nasal formulation of levocetirizine.

Means for Solving the Problem

This application provides an aqueous ophthalmic or nasal composition comprising levocetirizine or its salt as an active ingredient. In one aspect, an aqueous composition for ophthalmic or nasal administration comprising levocetirizine or its salt at a levocetirizine concentration of 0.05-0.5% (w/v) is provided. The aqueous composition for ophthalmic or nasal administration of the present application may further comprise a surface active agent and/or an organic acid salt. The composition may also comprise polyhexanide as a preservative. In another aspect, an aqueous composition for ophthalmic or nasal administration for use in the treatment of an allergic disease is provided. In the specification and claims, the expression "composition for ophthalmic or nasal administration" covers a composition that is used for both ophthalmic and nasal administration, a composition that is solely used for ophthalmic administration and also a composition that is solely used for nasal administration.

Effect of Invention

As evident from the working examples described below, the present application has enabled to provide a safe and stable aqueous composition for ophthalmic or nasal administration comprising levocetirizine. The provided composition is useful for the treatment of allergic diseases in the eyes or nose.

BRIEF DESCRIPTION OF DRAWINGS

FIG. 1 A graph showing the result of Example 4. The effects of aqueous ophthalmic composition comprising levocetirizine in a guinea pig histamine-induced allergic conjunctivitis model are shown.

EMBODIMENTS OF INVENTION

Levocetirizine used in the present application is a compound represented by the following chemical formula:

Examples of salts of levocetirizine used herein may include inorganic salts such as hydrochloride, sulfate, nitrate and phosphate, and organic salts such as acetate, citrate, tartrate and maleate.

The concentration of levocetirizine or its salt in the composition of the present application may vary depending on, for example, conditions of the allergic disease to be treated. In general, the composition may comprise levocetirizine or its salt at a levocetirizine concentration of about 0.05-0.5% (w/v), preferably about 0.05-0.25% (w/v), and especially, about 0.05-0.2% (w/v). For example, a composition comprising levocetirizine or its salt in an amount that provides about 0.05% (w/v), about 0.1% (w/v), about 0.12%

(w/v), about 0.15% (w/v) or 0.2% (w/v) of levocetirizine concentration is provided. The composition may be administered topically to the eyes or in the nose of the patient. One to several drops of the composition per one administration may be administered to an adult patient one to six times per day. In this specification and claims, the term "about" covers a ±20%, ±10% or ±5% value of the associated numerical value.

The surface active agent used in this application may preferably be a nonionic surface active agent. Examples may include polyoxyethylene sorbitan fatty acid esters such as polysorbate 80, polysorbate 60, polysorbate 40, polyoxyethylene sorbitan monolaurate, polyoxyethylene sorbitan triolate and polysorbate 65, and polyoxyethylene castor oil derivatives such as polyoxyethylene hydrogenated castor oil 50 and polyoxyethylene hydrogenated castor oil 60. Polysorbate 80 is particularly preferable. Nonionic surfactants may be used alone or in any combination of two or more.

Examples of the organic acid salts may include monocarboxylates such as acetate, trifluoroacetate, butyrate, palmitate and stearate, polyvalent carboxylates such as fumarate, maleate, succinate and malonate, oxycarboxylate such as gluconate, lactate, tartrate and citrate and organic sulfonates such as methanesulfonate, toluene sulfonate and tosylate. Citrate is particularly preferable. Examples of the citrates may include sodium citrate hydrate.

The amount of the surface active agent and/or organic acid salt in the composition of the present application may be determined based on the type of the surface active agent and/or organic acid salt as well as levocetirizine concentration. When it is used, the concentration of the surface active agent in the aqueous composition may be 0.0001-10% (w/v), preferably 0.05-5.0% (w/v) and especially 0.1-2.0% (w/v). In one embodiment, an aqueous composition comprising about 0.2% (w/v) of polysorbate 80 is provided.

When an organic acid salt is used, the concentration of the salt in the aqueous composition may be 0.01-10.0% (w/v), preferably 0.1-5.0% (w/v) and especially 0.4-2.5% (w/v). In one embodiment, an aqueous composition comprising about 0.85% (w/v) of sodium citrate hydrate is provided. In this embodiment, the concentration of sodium citrate in the aqueous composition is about 0.75% (w/v).

The surface active agents and/or organic acid salts described above may be used either individually or in combination of two or more.

In this application, the composition may further comprise a chelating agent. The "chelating agent" maybe any compound that can chelate a metal ion. Examples may include edetic acid (ethylenediaminetetraacetic acid) and a salt thereof, such as edetic acid, monosodium edetate, disodium edetate, trisodium edetate, tetrasodium edetate, dipotassium edetate, tripotassium edetate and tetrapotassium edetate. Disodium edetate hydrate (hereinafter referred simply to as "sodium edetate hydrate") is particularly preferable. The chelating agents may be used either individually or in combination of two or more.

In this application, the concentration of the chelating agent in the composition may be, for example, 0.0001-1% (w/v), preferably 0.0005-0.5% (w/v) and especially, 0.001-0.3% (w/v). In one embodiment, a composition comprising about 0.02% (w/v) of disodium edetate hydrate is provided. In this composition, the amount of disodium edetate is about 0.018% (w/v).

The pH of the aqueous composition may be in a range that is usually employed for ophthalmic or nasal preparations. Usually, the pH of the aqueous composition may be in the range of 4.0-9.0, and preferably 5.0-8.0. For example, the pH of the composition may be adjusted to about 7.0. The pH of the composition may be adjusted by adding a pH adjusting agent such as hydrochloride or sodium hydroxide.

The composition of the present application may comprise a preservative. Examples of the preservatives may include polyhexamethylene biguanide derivatives such as polyhexanide hydrochloride, polydronium chloride derivatives such as polydronium chloride, polyquaternium chloride derivatives such as polyquaternium chloride, chlorhexidine derivatives such as chlorhexidine, benzalkonium chloride derivatives such as benzalkonium chloride, benzethonium chloride derivatives such as benzethonium chloride, chlorobutanol and sorbic acid. Polyhexanide hydrochloride is preferably used. The concentration of the preservative in the aqueous composition is not particularly limited as long as it is within the range accepted for ophthalmic and nasal preparations. When polyhexanide hydrochloride is used as the preservative, the concentration of the compound in the composition may be 0.000005-0.002% (w/v), preferably 0.00001-0.001% (w/v) and especially 0.00005-0.0005% (w/v). In one embodiment, an aqueous composition may be prepared by adding polyhexanide hydrochloride such that the calculated concentration of polyhexanide hydrochloride in the composition is about 0.000092% (w/v). In this embodiment, the concentration of polyhexanide may be reduced due to filtration and adsorption onto the container during the manufacture and an ophthalmic composition comprising about 0.00008% (w/v) polyhexanide may be provided. The preservatives may be used either individually or in combination of two or more.

The osmotic pressure ratio of the aqueous composition of the present application may be adjusted to 0.7-1.3, preferably 0.9-1.1, and for example, about 1. An isotonic agent such as potassium chloride, sodium chloride, glycerin, glucose and D-mannitol may appropriately be added to adjust the osmotic pressure ratio. A thickening agent such as carboxyvinyl polymer, povidone, polyvinyl alcohol, macrogol 4000, hydroxyethyl alcohol, hypromellose, methylcellulose and glycerin may also be added to the composition of this application.

The composition of this application may further comprise any other pharmaceutically active agent as long as the agent is not deteriorate the purpose of the present invention.

The present application is further explained in more detail with the following working examples and formulation examples. Those examples should never be used for limiting the scope of this application. In the followings, all "%" represents weight/volume % (% w/v).

EXAMPLES

Example 1

Human Eye Irritation Study

Ophthalmic solutions shown in Table 1 were instilled to human eyes and irritation caused by the instillation was evaluated.

TABLE 1

| ingredients | \multicolumn{11}{c}{concentration (mg/mL)} |
|---|---|---|---|---|---|---|---|---|---|---|---|
| | 1 | 2 | 3 | 4 | 5 | 6 | 7 | 8 | 9 | 10 | 11 |
| levocetirizine hydrochloride* | 5.00 | 5.00 | 5.00 | 2.38 | 2.38 | 2.00 | 2.38 | 2.00 | 2.00 | 1.19 | 1.19 |
| Polysorbate 80 | — | 20.0 | — | — | 2.00 | — | — | — | — | — | 1.00 |
| povidone(K25) | — | — | 30.0 | — | — | 20.0 | — | — | — | — | — |
| Lipidure ® | — | — | — | — | — | — | 20.0 | — | — | — | — |
| hypromellose | — | — | — | — | — | — | — | 3.00 | — | — | — |
| glycerin | — | — | — | — | — | — | — | — | 25.0 | — | — |
| sodium chloride | \multicolumn{11}{c}{an amount for adjusting the osmotic pressure ratio of the composition to 1} |
| sodium hydroxide | \multicolumn{11}{c}{an amount for adjusting the pH of the composition to 7} |

*5.00 mg/mL and 2.00 mg/mL represent 0.5% and 0.2% of levocetirizine hydrochloride concentration, respectively
2.38 mg/mL and 1.19 mg/mL represent 0.2% and 0.1% of levocetirizine concentration, respectively Eye irritation was evaluated by the following criteria
Score 0: No irritation or discomfort
Score 1: Discomfort
Score 2: Slight irritation
Score 3: Pain
Score 4: Strong irritation
Results are summarized in Table 2

TABLE 2

| | \multicolumn{11}{c}{Eye Irritation} |
|---|---|---|---|---|---|---|---|---|---|---|---|
| | \multicolumn{11}{c}{Composition No.} |
| | 1 | 2 | 3 | 4 | 5 | 6 | 7 | 8 | 9 | 10 | 11 |
| Average | 3.5 | 0.7 | 0 | 0.7 | 0 | 0 | 0.4 | 0.5 | 0.3 | 0.4 | 0 |
| (n) | (3) | (3) | (1) | (7) | (6) | (9) | (7) | (4) | (6) | (5) | (5) |

The composition comprising about 0.5% of levocetirizine and no additive caused high irritation. The eye irritation was suppressed by adding polysorbate 80 or povidone. The composition comprising about 0.2% or less of levocetirizine and no additive caused less eye irritation. Improvements were found in the composition comprising about 0.2% or less of levocetirizine and polysorbate 80 or povidone, i.e. no irritation or discomfort was reported.

Example 2

Stability Test

Ophthalmic solutions comprising 1% of levocetirizine hydrochloride were prepared, one with no additive, one added with sodium edetate hydrate and one added with sodium citrate hydrate. The solutions were left at room temperatures for 4 weeks and then, precipitation of levocetirizine hydrochloride was observed by microscope. Results are shown in Table 3.

TABLE 3

| Additive | amount (mg/mL) | Precipitation after 4 weeks at room temperatures |
|---|---|---|
| None | 0 | + |
| Sodium edetate hydrate | 1.27 | + |
| Sodium citrate hydrate | 8.50 | − |

In the levocetirizine ophthalmic solution comprising no additive and that added with sodium edetate hydrate, precipitations were observed, while no precipitation was observed in the solution containing sodium citrate hydrate.

Example 3

Stability Test

Ophthalmic solutions comprising levocetirizine hydrochloride in an amount to give 0.2% of levocetirizine concentration with additives shown in Table 4 were prepared. The precise amounts of levocetirizine and total impurities in each solution were measured by HPLC. The "total impurities" represents total amount of levocetirizine decomposition products and impurities derived from the additives.

TABLE 4

| ingredients | \multicolumn{7}{c}{compositions (mg/mL)} |
|---|---|---|---|---|---|---|---|
| | 1 | 2 | 3 | 4 | 5 | 6 | 7 |
| levocetirizine hydrochloride | 2.38 | 2.38 | 2.38 | 2.38 | 2.38 | 2.38 | 2.38 |
| polysorbate 80 | — | 2.00 | 2.00 | 2.00 | 1.00 | 1.00 | 1.00 |
| sodium edetate hydrate | — | — | 0.20 | — | — | 0.20 | — |
| sodium citrate hydrate | — | — | 8.50 | 8.50 | 8.50 | 8.50 | 8.50 |
| povidone(K25) | — | — | — | — | — | 5.00 | 5.00 |
| macrogol 4000 | — | — | — | — | 5.00 | 5.00 | 5.00 |
| polyhexanide hydrochloride solution* | 0.0046 | 0.0046 | 0.0046 | 0.0046 | — | — | — |
| benzalkonium chloride | — | — | — | — | 0.2 | 0.2 | 0.2 |
| sodium chloride | \multicolumn{7}{c}{an amount for adjusting the osmotic pressure ratio of the composition to 1} |
| sodium hydroxide | \multicolumn{7}{c}{an amount for adjusting the pH of the solution composition 7} |

*The amount 20% polyhexanide hydrochloride solution fed to the composition. The concentration of polyhexanide hydrochloride in the ophthalmic solution was about 0.00008% (w/v).

Results are shown in Table 5.

TABLE 5

| composition | Start | | | 50° C./75% RH, one month | | |
|---|---|---|---|---|---|---|
| | pH | levocetirizine amount (remaining %) | Total Impurities | pH | levocetirizine amount* (remaining %) | Total Impurities |
| 1 | 6.98 | 99.22 (100.00) | 0.00 | 6.97 | 99.04 (99.82) | 0.00 |
| 2 | 6.92 | 99.20 (100.00) | 0.00 | 6.86 | 99.24 (100.04) | 0.16 |
| 3 | 6.88 | 97.92 (100.00) | 0.00 | 6.87 | 98.40 (100.49) | 0.11 |
| 4 | 6.94 | 97.67 (100.00) | 0.00 | 6.93 | 98.40 (100.75) | 0.16 |
| 5 | 6.97 | 100.54 (100.00) | 0.35 | 6.98 | 98.30 (97.77) | 0.61 |
| 6 | 6.97 | 99.69 (100.00) | 0.41 | 6.93 | 97.13 (97.43) | 1.42 |
| 7 | 6.99 | 100.87 (100.00) | 0.58 | 6.98 | 100.42 (99.55) | 1.13 |

*water corrected unit % (levocetirizine amount and total impurities)

In composition Nos. 5, 6 and 7, i.e. compositions to which povidone and/or macrogol 4000 and benzalkonium chloride were added, increases of total impurities were observed.

Example 4

Stability Test

Compositions comprising the same additives as composition No. 3 in Example 3 and different concentrations of levocetirizine chloride were prepared and subjected to the stability test.

TABLE 6

| ingredients | compositions (mg/mL) | | | |
|---|---|---|---|---|
| | 0.05% | 0.1% | 0.2% | 0.5% |
| levocetirizine hydrochloride | 0.594 | 1.19 | 2.38 | 5.94 |
| polysorbate 80 | 2.00 | 2.00 | 2.00 | 2.00 |
| sodium edetate hydrate | 0.20 | 0.20 | 0.20 | 0.20 |
| sodium citrate hydrate | 8.50 | 8.50 | 8.50 | 8.50 |
| polyhexanide hydrochloride solution* | 0.0046 | 0.0046 | 0.0046 | 0.0046 |
| sodium chloride | an amount for adjusting the osmotic pressure ratio of the composition to 1 | | | |
| sodium hydroxide | an amount for adjusting the pH of the composition to 7 | | | |

*The amount of 20% polyhexanide hydrochloride solution fed to the composition. The concentration of polyhexanide hydrochloride in the composition was about 0.00008% (w/v).

Results are shown in Table 7

TABLE 7

Stability test with various concentration of levocetirizine compositions
Acceleration test: 40° C./20% RH

| composition | Start | | | one month | | | six months | | |
|---|---|---|---|---|---|---|---|---|---|
| | pH | Levocetirizine amount (remaining %) | Total Impurities | pH | Levocetirizine amount* (remaining %) | Total Impurities | pH | Levocetirizine amount* (remaining %) | Total Impurities |
| 0.05% | 6.99 | 100.37 (100.00) | 0.00 | 6.98 | 98.92 (98.56) | 0.00 | 6.96 | 98.93 (98.67) | 0.00 |
| 0.1% | 7.00 | 100.05 (100.00) | 0.00 | 6.99 | 99.38 (99.33) | 0.00 | 6.96 | 99.63 (99.69) | 0.00 |
| 0.2% | 6.99 | 99.00 (100.00) | 0.00 | 6.99 | 99.52 (100.53) | 0.00 | 6.97 | 99.85 (100.96) | 0.00 |
| 0.5% | 7.01 | 99.44 (100.00) | 0.00 | 7.02 | 100.39 (100.96) | 0.00 | 6.99 | 100.11 (100.78) | 0.00 |

* water corrected unit % (levocetirizine amount and total impurities)

In the six months acceleration test, compositions with all levocetirizine concentrations were stable.

Formulation Example

Formulation Example 1

TABLE 8

(1 mL solution)

| | |
|---|---|
| levocetirizine hydrochloride | 0.594 mg |
| sodium citrate hydrate | 8.50 mg |
| polysorbate 80 | 2.00 mg |
| sodium chloride | 6.00 mg |
| sodium edetate hydrate | 0.20 mg |
| polyhexanide hydrochloride | 0.00092 mg* |
| sodium hydrate | an amount adjusting the pH of the composition to 7 |
| purified water | balance |

*amount added to give a concentration of about 0.00008% in the solution

Levocetirizine hydrochloride and the other ingredients were added to purified water and mixed well to give an aqueous composition for ophthalmic or nasal administration of formulation example 1.

Formulation Example 2

Three additional aqueous compositions for ophthalmic or nasal administration containing the same ingredients as formulation example 1 except for the concentration of levocetirizine hydrochloride per 1 ml of the solution was adjusted to 1.19 mg, 2.38 mg or 5.94 mg were prepared.

Example 5

Pharmacology Test

Experimental allergic conjunctivitis was induced in guinea pigs by administering histamine to the conjunctiva of the animals. The effects of the formulations prepared in Example 4, comprising levocetirizine hydrochloride in an amount corresponding to 0.05%, 0.1% and 0.2% of levocetirizine were examined. The solution containing all ingredients but not levocetirizine hydrochloride was used as negative control, and Alesion (registered trademark) 0.05% ophthalmic solution (Santen Pharmaceuticals, co. ltd.) was used as positive control. Each test solutions were instilled to the eyes of the animals 6 hours before the instillation of histamine. 50 μL of histamine solution (100 μg/mL) was administered to the conjunctiva and 1 mL/kg of evans blue dye (10 mg/mL) was intravenously injected to the animals. Thirty minutes after administration of histamine, the amounts of evans blue dye in the conjunctiva were measured. Results are shown in FIG. 1.

Effects of levocetirizine ophthalmic solutions were evaluated using the evans blue dye leakage as an index of inflammation. Levocetirizine 0.05-0.2% solutions were effectively suppressed conjunctivitis compared to the negative control. This effects were superior to that obtained by the commercially available ophthalmic solution for allergic eye diseases.

What is claimed is:

1. An aqueous composition for ophthalmic or nasal administration, which comprises levocetirizine or its salt as an active ingredient and polyhexanide hydrochloride as a preservative, wherein a concentration of levocetirizine or its salt in the composition as levocetirizine is 0.05-0.5% (w/v) and a concentration of polyhexanide hydrochloride in the composition is 0.00001-0.001% (w/v).

2. The composition according to claim 1, which further comprises a surface active agent and an organic acid salt.

3. The composition according to claim 1, wherein the composition further comprises a surface active agent.

4. The composition according to claim 3, wherein the composition comprises polysorbate 80 as a surface active agent.

5. The composition according to claim 1, wherein the composition further comprises an organic acid salt.

6. The composition according to claim 5, wherein the composition comprises citric acid salt as an organic acid salt.

7. An aqueous composition, comprising about 0.05 to about 0.5% (w/v) of levocetirizine or a salt thereof based on the amount of levocetirizine, about 0.00001% to about 0.001% (w/v) of polyhexanide hydrochloride, about 0.1% to about 2.0% (w/v) of polysorbate 80, about 0.4% to about 2.5% (v/w) of a citric acid salt, and about 0.001 to about 0.3% (w/v) of disodium edetate.

8. The composition according to claim 3, wherein a concentration of the surface active agent in the composition is 0.1-2.0% (w/v).

9. The composition according to claim 5, wherein a concentration of the organic acid salt in the composition is 0.4-2.5% (w/v).

10. The composition according to claim 1, which is for the ophthalmic use.

11. The composition according to claim 1, wherein the concentration of polyhexanide hydrochloride is 0.00005-0.0005% (w/v).

12. The composition according to claim 1, further comprising about 0.1-2.0% (w/v) of polysorbate 80, about 0.4-2.5% (v/w) of a citric acid salt, and about 0.001-0.3% (w/v) of disodium edetate.

13. The composition according to claim 12, which comprises about 0.2% (w/v) of polysorbate 80, about 0.75% (v/w) of sodium citrate, about 0.018% (w/v) of disodium edetate, and about 0.00005-0.0005% (w/v) of polyhexanide hydrochloride.

* * * * *